(12) United States Patent
Shields

(10) Patent No.: US 11,554,252 B2
(45) Date of Patent: Jan. 17, 2023

(54) WINGUIDE NEEDLE GUIDE

(71) Applicant: Sam Shields, Reno, NV (US)

(72) Inventor: Sam Shields, Reno, NV (US)

( * ) Notice: Subject to any disclaimer, the term of this patent is extended or adjusted under 35 U.S.C. 154(b) by 1182 days.

(21) Appl. No.: 16/066,281

(22) PCT Filed: Feb. 12, 2017

(86) PCT No.: PCT/US2017/017587
§ 371 (c)(1),
(2) Date: Jun. 26, 2018

(87) PCT Pub. No.: WO2017/142820
PCT Pub. Date: Aug. 24, 2017

(65) Prior Publication Data
US 2019/0046770 A1 Feb. 14, 2019

Related U.S. Application Data

(60) Provisional application No. 62/297,922, filed on Feb. 21, 2016.

(51) Int. Cl.
*A61M 25/01* (2006.01)
*A61M 25/09* (2006.01)
(Continued)

(52) U.S. Cl.
CPC ....... *A61M 25/0136* (2013.01); *A61B 8/0841* (2013.01); *A61M 5/427* (2013.01);
(Continued)

(58) Field of Classification Search
CPC .............. A61M 25/0136; A61M 25/06; A61M 25/09041; A61M 25/09; A61M 25/0138;
(Continued)

(56) References Cited

U.S. PATENT DOCUMENTS 5,159,861 A * 11/1992 Anderson ............... A61B 17/22
606/1
5,185,004 A * 2/1993 Lashinski ......... A61M 25/0136
604/533
(Continued)

*Primary Examiner* — Kevin C Sirmons
*Assistant Examiner* — Alexandra Lalonde
(74) *Attorney, Agent, or Firm* — Jonathan D Feuchtwang

(57) ABSTRACT

Disclosed is a device for facilitating placement of a central line in a patient, said device comprising: a housing having proximal and distal ends and a central portion therebetween, said housing having an upper portion and a lower portion; a handgrip provided on the proximal end of the housing, said handgrip having at least one of a channel and a through hole extending from the proximal end to the central portion, wherein the channel or through hole is sized to receive a guidewire; a feeder tip receiver provided on a proximal end of the handgrip in communication with the channel or through hole in said handgrip; a stabilizer provided on the lower portion of said housing; a luer slip tip provided on the distal end of the housing, said luer slip tip having a mounting portion for attachment to a needle hub, said luer slip tip having a lumen aligned with the channel or through hole in said handgrip; and a wire slide platform provided on the central portion of the housing.

18 Claims, 18 Drawing Sheets

(51) Int. Cl.
   *A61M 5/42*     (2006.01)
   *A61M 25/06*    (2006.01)
   *A61B 8/08*     (2006.01)

(52) U.S. Cl.
   CPC .... *A61M 25/0102* (2013.01); *A61M 25/0108* (2013.01); *A61M 25/06* (2013.01); *A61M 25/09* (2013.01); *A61M 25/09041* (2013.01); *A61M 25/0172* (2013.01); *A61M 2025/09116* (2013.01)

(58) Field of Classification Search
   CPC .............. A61M 25/01; A61M 25/0102; A61M 25/0172; A61M 5/427; A61M 25/0169; A61M 2025/09116; A61M 2025/09125; A61M 2025/0177; A61M 2025/018
   See application file for complete search history.

(56) References Cited

U.S. PATENT DOCUMENTS

| | | | | |
|---|---|---|---|---|
| 5,827,202 A | * | 10/1998 | Miraki | A61M 25/09041 604/95.01 |
| 6,626,869 B1 | * | 9/2003 | Bint | A61M 25/09041 604/164.01 |
| 2003/0036712 A1 | * | 2/2003 | Heh | A61M 25/09041 604/95.04 |
| 2010/0305474 A1 | * | 12/2010 | DeMars | B65H 75/364 242/588.2 |
| 2012/0078231 A1 | * | 3/2012 | Hoshinouchi | A61M 25/09041 604/528 |
| 2016/0015943 A1 | * | 1/2016 | Belson | A61M 25/09 604/164.08 |

* cited by examiner

WINGUIDE NEEDLE GUIDE

CROSS-REFERENCE TO RELATED APPLICATIONS

This application claims priority to and the benefit of U.S. Provisional Patent Application No. 62/297,922 entitled "WINGUIDE" filed Feb. 21, 2016.

BACKGROUND

The present invention relates to a device for placing the central line or PICC line in a patient using ultrasound guidance and a method of using the same.

Conventional central line placement requires the clinician to use a syringe and needle technique to blindly find the central vein to obtain access. This technique is termed the Seldinger Technique in the medical literature. The success of this technique is user dependent and has a fairly prolonged learning curve. The technique is also known to have some significant complications. To mitigate the learning curve and to decrease the complication rate, ultrasound has recently been used to visualize the blood vessel.

Ultrasound guided central line placement requires the same Seldinger technique. If done properly, the ultrasound guided central line technique ensures proper placement of the central line into the appropriate vessel under direct visualization. With this knowledge the clinician can be sure he is in the correct vessel as well as document that there are no complications related to venipuncture. However, the ultrasound guided central line placement technique is not without its difficulties. Ultrasound is a relatively new technology for bedside point of care use for central venous access. Ultrasound in medicine, until recently, has been relegated to the ultrasound technician to perform the procedure and the radiologist to interpret the results. Bedside use by the practicing physician has been limited to a few specialties such as obstetrics ultrasound usage in the office. Emergency medicine is now pioneering the field of point of care ultrasound use by the clinician. Unfortunately many practicing physicians have no formal training in the use of ultrasound to guide the placement of the central line.

When performing the ultrasound guided central line placement technique, the clinician must hold the ultrasound probe in the non-dominant hand and hold the needle-on-syringe in the dominant hand while aspirating blood to signify vein puncture and entering the vessel. Once the vessel is entered the clinician must drop the ultrasound probe with the non-dominant hand, and grasp the hub of the needle that is currently inserted into the vein with the same non-dominant hand. The clinician then must remove the syringe and insert the guidewire while holding the needle hub perfectly stable. Once the ultrasound probe is dropped the clinician no longer has visualization of the position of the needle. Without perfect stabilization of the needle hub, access to the central vessel can easily be lost and the guidewire may be difficult or impossible to thread into the central vessel.

The wire-in-needle (WIN) technique has been designed to obviate this difficulty during ultrasound central line placement. With the WIN technique the guidewire is threaded into the needle and no syringe is used. The needle is grasped along with the guidewire where it inserts into the needle hub. This is used as a single unit. The ultrasound transducer is placed in the appropriate position with the non-dominant hand as in the standard ultrasound guided central line procedure. This time, however, the needle and wire are inserted as a unit and once the needle is seen within the vessel the guidewire is immediately threaded through the needle into the vessel under direct visualization of the ultrasound. At no point is there any loss of direct visualization of the procedure. Therefore with constant visualization the clinician can be assured of placement and also be assured no complications occurred during the procedure.

The WIN technique has its own technical difficulties. With this technique the physician needs to hold the needle at the hub of the needle and then try to advance the needle in this fashion. This is much like holding a pencil by the eraser end. This does not allow multiple positions of the physician relative to the needle and the patient to be used. It is also technically difficult to learn this procedure. It requires holding the needle firmly in place at the small hub of the needle with the index finger and thumb while simultaneously attempting to advance the guidewire with the remaining fingers. Alternatively, the physician can let go of the needle and attempt to advance the guidewire. However this is not considered safe as there could be needle movement if there is not sufficient adipose tissue and/or thick skin to hold a needle in place. The needle can then move around and exit the vessel or cause injury in this fashion.

SUMMARY OF THE INVENTION

In a first aspect, disclosed is a device for facilitating placement of a central line in a patient. The device comprises a housing having proximal and distal ends and a central portion therebetween, the housing having an upper portion and a lower portion. The device includes a handgrip provided on a proximal end of the housing. The handgrip has at least one of a channel and a through hole extending from the proximal end to the central portion, wherein the channel or through hole is sized to receive a guidewire. A feeder tip receiver is provided on a proximal end of the handgrip in communication with the channel or through hole in the handgrip. A stabilizer is provided on a lower portion of the housing. A Luer slip tip is provided on a distal end of the housing, the Luer slip tip having a mounting portion for attachment to a needle hub, the Luer slip tip having a lumen aligned with the channel or through hole in the handgrip. A wire slide platform is provided on the central portion of the housing.

The above-described device may include a thumb base ramp provided on the housing proximate a proximal end of the wire slide platform. The thumb base ramp may angle downward towards the wire slide platform. The thumb base ramp may include non-slip features.

The above-described device may include a thumb tip ramp provided on the housing proximate a distal end of the wire slide platform. The thumb tip ramp may angle upward away from the wire slide platform. The device may further include a cleaning edge provided on adjacent the thumb tip ramp. The device may further include a needle assembly having a hollow sharpened needle having a lumen extending therethrough, the need attached to a hub, the hub removably attached to the Luer slip tip.

The above-described device may further include a guidewire acceptor having a lumen aligned and in communication with the Luer slip tip lumen and the channel or through hole in the handgrip. The guidewire acceptor may be funnel shaped with a wide mouth which tapers to a narrow lumen, wherein the guidewire acceptor is configured to receive a guidewire fed from the feeder tip receiver through the handgrip, on the wire slide platform and out the Luer slip tip lumen.

The thickness of the handgrip in the above-described device may gradually increase from the proximal to the distal end.

The above-identified device may further include a transparent flashback reservoir in the thumb tip ramp, the reservoir is in fluid communication with the Luer slip tip lumen.

The above-identified device may further include a backflow preventer provided in fluid communication with the Luer slip tip lumen, the backflow preventer comprising a gasket configured to surround and engage a guidewire.

Also disclosed is a method for using the above-described device. The method includes a step of providing a needle assembly having a hub attached to a hollow sharpened needle with a lumen extending therethrough. The needle hub is attached to the Luer slip tip.

The method includes a step of providing a guidewire assembly having a guidewire in a coiled sheath, the coiled sheath including a guidewire feeder tip.

The guidewire feeder tip is inserted into a guidewire acceptor provided in communication with the Luer slip tip lumen. The guidewire is advanced from the sheath through the guidewire feeder tip into the needle lumen. The guidewire feeder tip is removed from the guidewire acceptor without withdrawing the guidewire from the needle lumen and inserting the guidewire feeder tip into the feeder tip receiver.

The method includes a step of identifying a blood vessel to be cannulated using an ultrasound transducer. The user grasps the device with their hand and uses the needle to puncture the skin and advance towards the lumen of the vein while visualizing using ultrasound. The needle is inserted into the lumen of the vein. The user stabilizes the device by compressing his/her long and index fingers of the user's hand onto the stabilizer and placing a thumb tip of the user's hand in a vertical position at the thumb base ramp. The user compresses the guidewire on the wire slide platform with the thumb tip, and advances the guidewire on the wire slide platform to the thumb tip ramp.

The user advances his/her thumb tip up the thumb tip ramp to advance the guidewire into the lumen of the vein. The user then releases thumb pressure on guidewire and slowly backs the needle out of the skin, while compressing the guidewire on the skin with the other hand to expose the guidewire entering the skin and vein.

These and other embodiments are described in further detail in the following description related to the appended drawing figures.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 2A is grasped;

FIG. 2A is stabilized and guidewire is advanced on the wire slide platform 103;

DETAILED DESCRIPTION

Specific embodiments of the disclosed device, delivery system, and method will now be described with reference to the drawings. Nothing in this detailed description is intended to imply that any particular component, feature, or step is essential to the invention.

Throughout this disclosure the term proximal is intended to denote the end or portion nearest the user and the term distal is intended to denote the end or portion furthest away from the user.

The WINGUIDE of the present invention is a device designed specifically to allow the clinician to gain real-time visual access to the venous/arterial system and maintain this visualization while inserting a guidewire into the lumen of a blood vessel. The guide has several unique features which are explained in detail below.

Figure 1A:
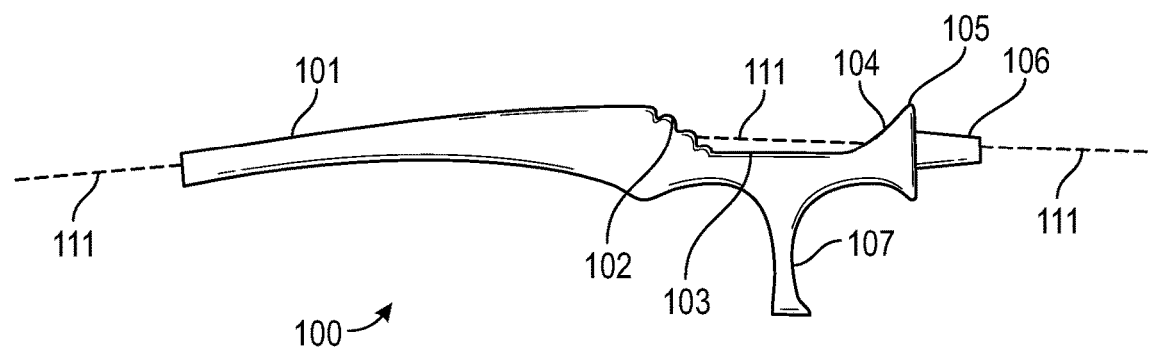
FIGS. 1A-1D are side, top, front and back views of WINGUIDE 100.
Figure 1B:
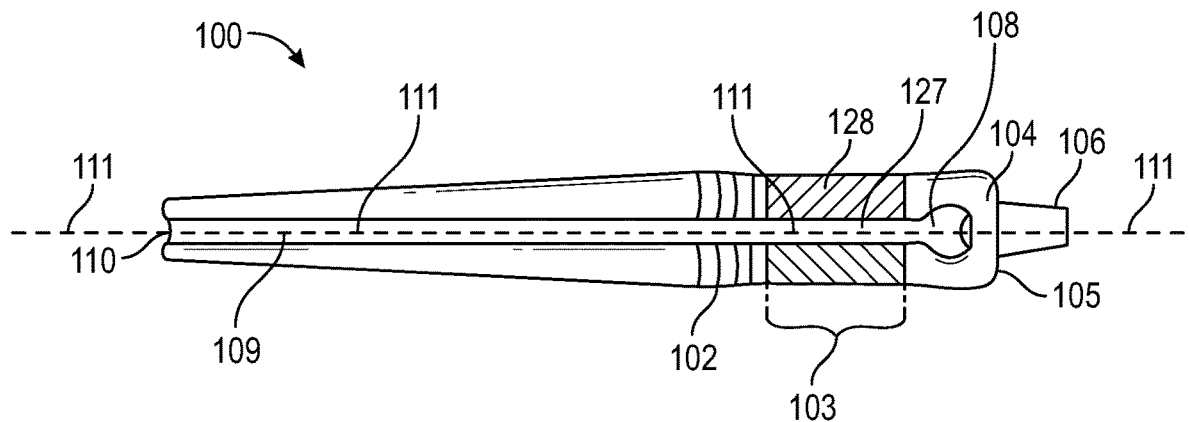
Figure 1C:
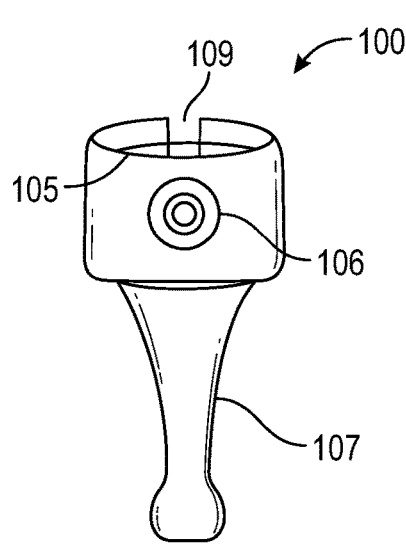
Figure 1D:
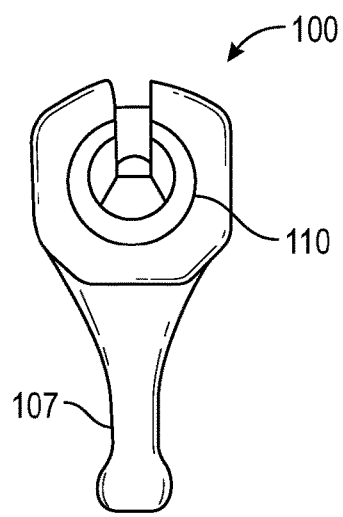
Figure 1E:
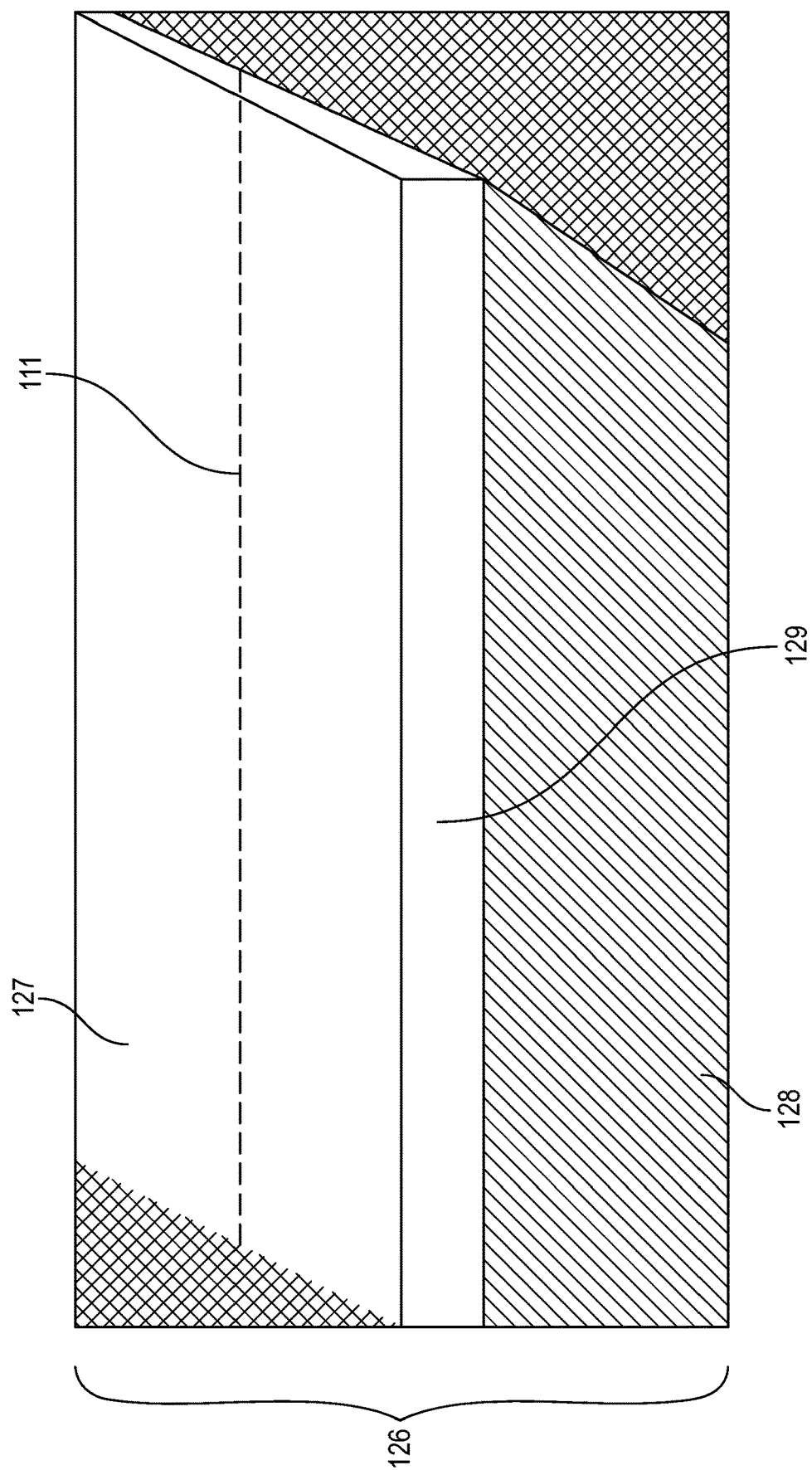
FIG. 1E is a cross-section 126 of the wire slide platform 103.

FIGS. 1A-1D are side, top, front and back views of WINGUIDE 100. FIG. 1E is a sectional view of the wire slide platform.

Luer slip tip 106 is provided on a distal end of the WINGUIDE 100. A conventional needle 115 (FIG. 3A) having needle hub 114 is attached to the Luer slip tip 106. The needle 115 is hollow and has a sharp end 116 to pierce the skin and deliver a guidewire into a blood vessel. The needle 115 has a lumen sized to receive a conventional guidewire 111.

Figure 3A:
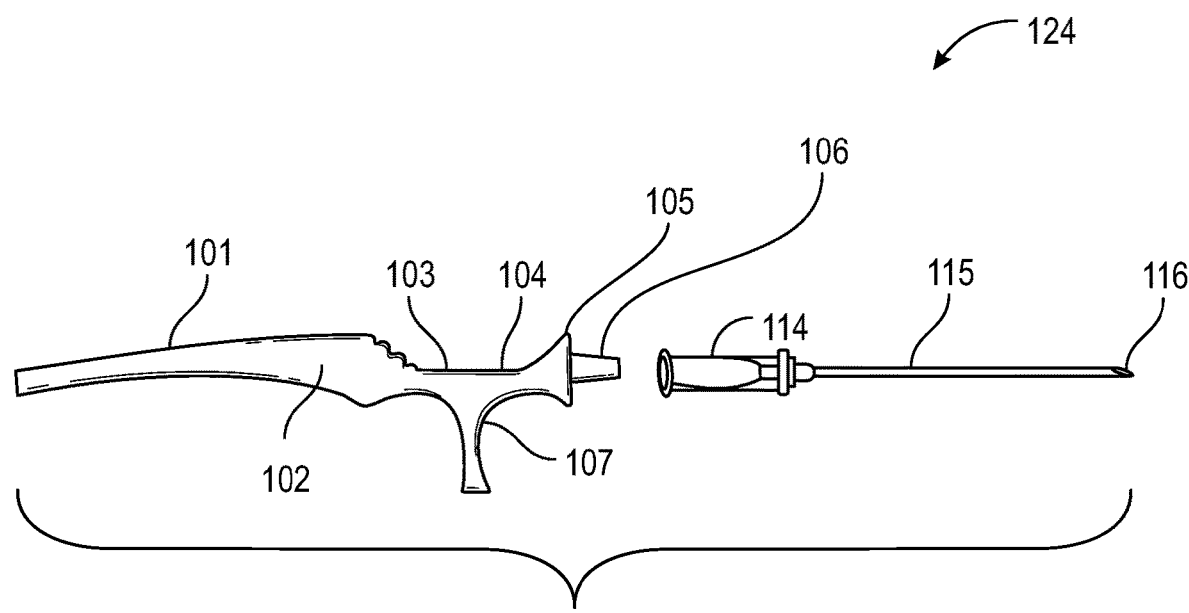
FIGS. 3A and 3B are side views of the device shown in FIG. 1A or FIG. 2A with guidewire coil 119 and needle 115.
Figure 3B:
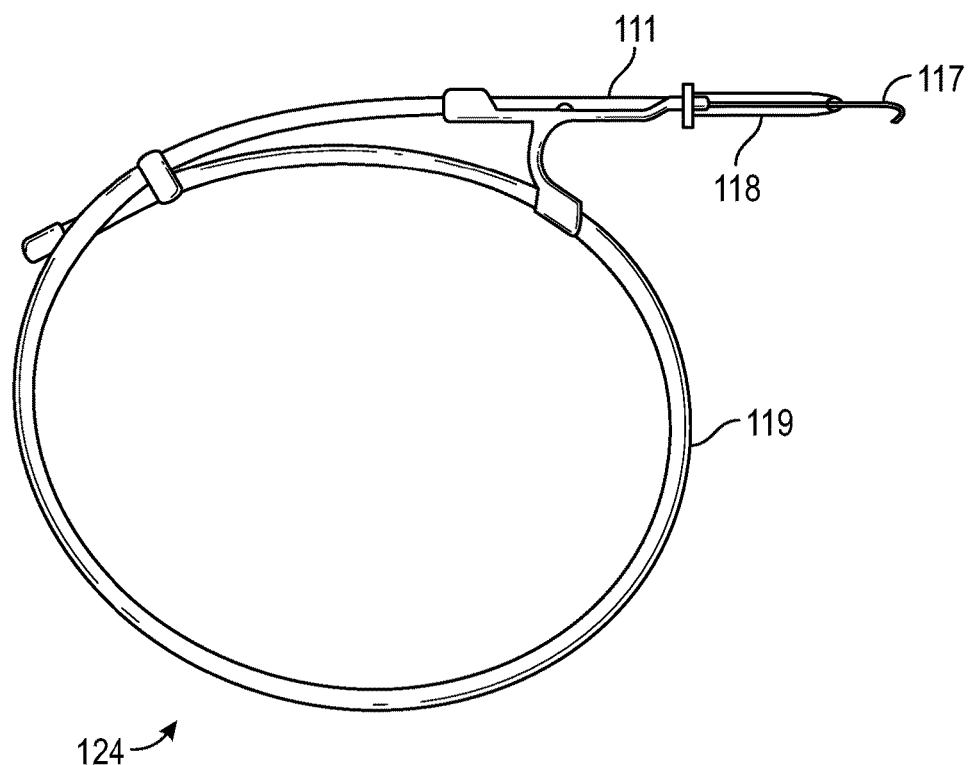
Figure 5:
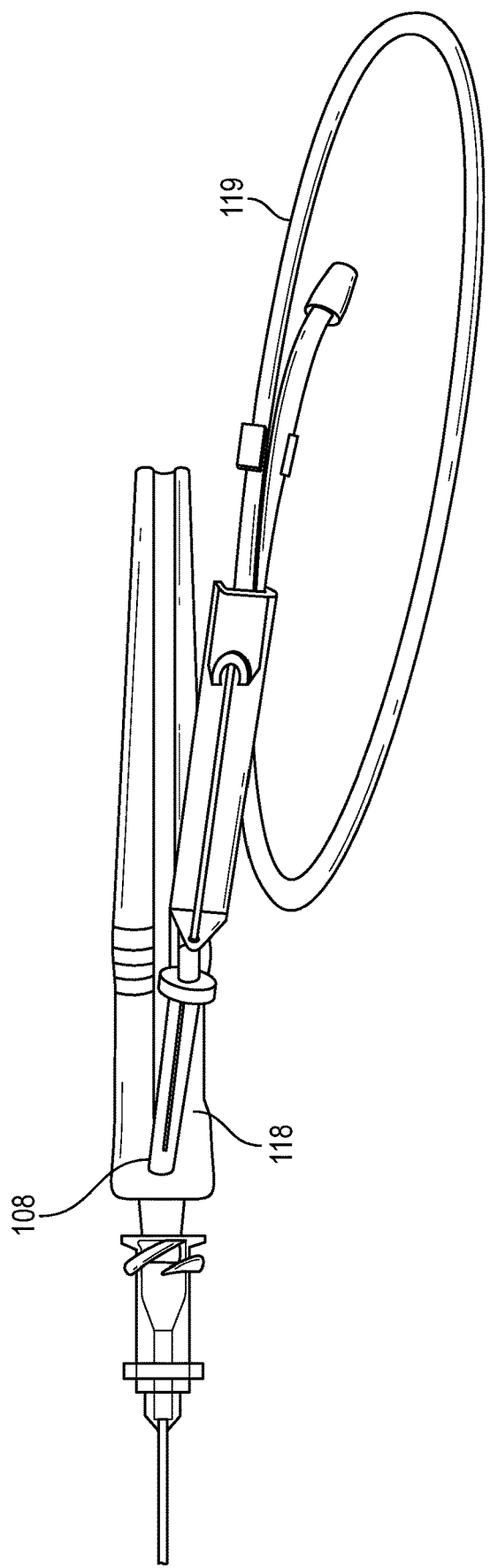
FIG. 5 is an illustration showing how the central line guidewire coil 119 having a feeder tip 118 is attached to the device shown in FIG. 1A or FIG. 2A.

The WINGUIDE is adapted to be used with a standard central line tray which includes a central line guidewire coil 119 having a feeder tip 118 (FIGS. 3A, 3B and 5). The term central line as used in this specification is intended to include both a central line and a PICC (peripherally inserted central catheter). The present invention is useful for any access using the standard Seldinger technique. Guidewire 111 is stored in the coil 119 and is dispensed therefrom through feeder tip 118.

GUIDEWIRE FEEDER TIP RECEIVER 110: The WINGUIDE 100, 124, 125 has a guidewire feeder tip receiver 110 at the proximal end of the device. This feeder tip receiver 110 is designed to accept the feeder tip 118 from a central line coil 119 from a standard central line tray (FIGS. 3A, 3B and 5). The feeder tip receiver locks the guidewire feeder tip 118 in place on the WINGUIDE 100 and allows for stabilization of the guidewire coil 119 onto the device. The coil 119 can also be removed from the guidewire feeder tip 118 assembly to ease the maneuverability of the WINGUIDE 100 if the clinician chooses. Incorporating the guidewire feeder tip assembly 118/119 into the WINGUIDE 100 allows the wire to exit the device without ever touching the palm which ensures no added resistance during advancement of the guidewire 111.

LUER SLIP TIP 106: The WINGUIDE 100, 124, 125 has a Luer slip tip 106 that is used for attachment to the needle 115. The Luer slip tip 106 allows the clinician to adjust the needle bevel 116 alignment to his/her personal preferred position, prior to puncture of the skin, by simply rotating the needle 115. The Luer slip tip 106 accepts standard needles 115 for Seldinger Technique.

GRIP 101: The WINGUIDE 100 includes a grip or handle 101. Grip 101 is designed to ergonomically fit in a palm of the user's hand. The grip 101 may be tapered, and may include anti-slip features such as knurling or the like. The proximal end of the grip 101 ends in the guidewire feeder tip receiver 110.

Figure 15:
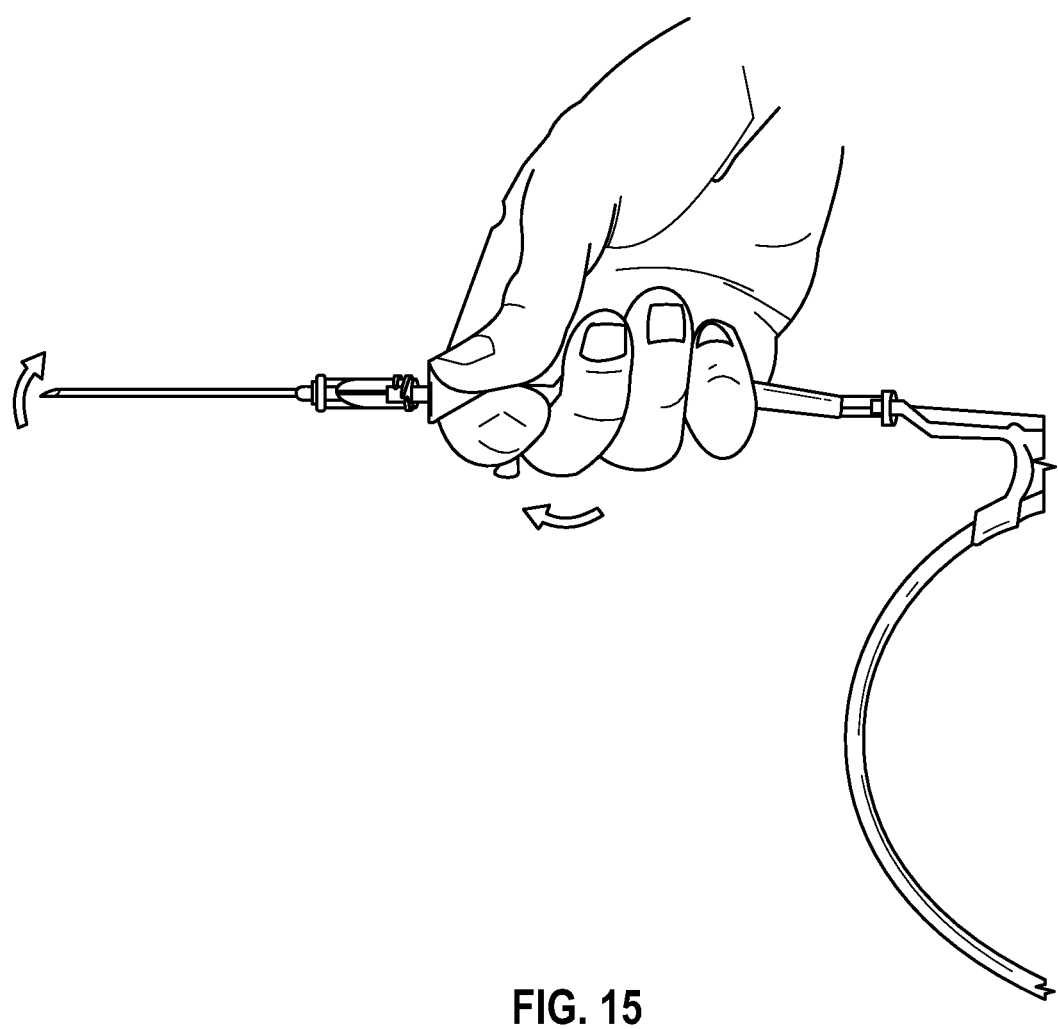
FIGS. 15 and 16 are illustrations showing how the device shown in FIG. 1A or FIG. 2A can be adjusted in an upward or downward fashion by using the stabilizer and pulling the index finger backward or pushing on the middle finger for precise placement of the needle tip during insertion.
Figure 16:
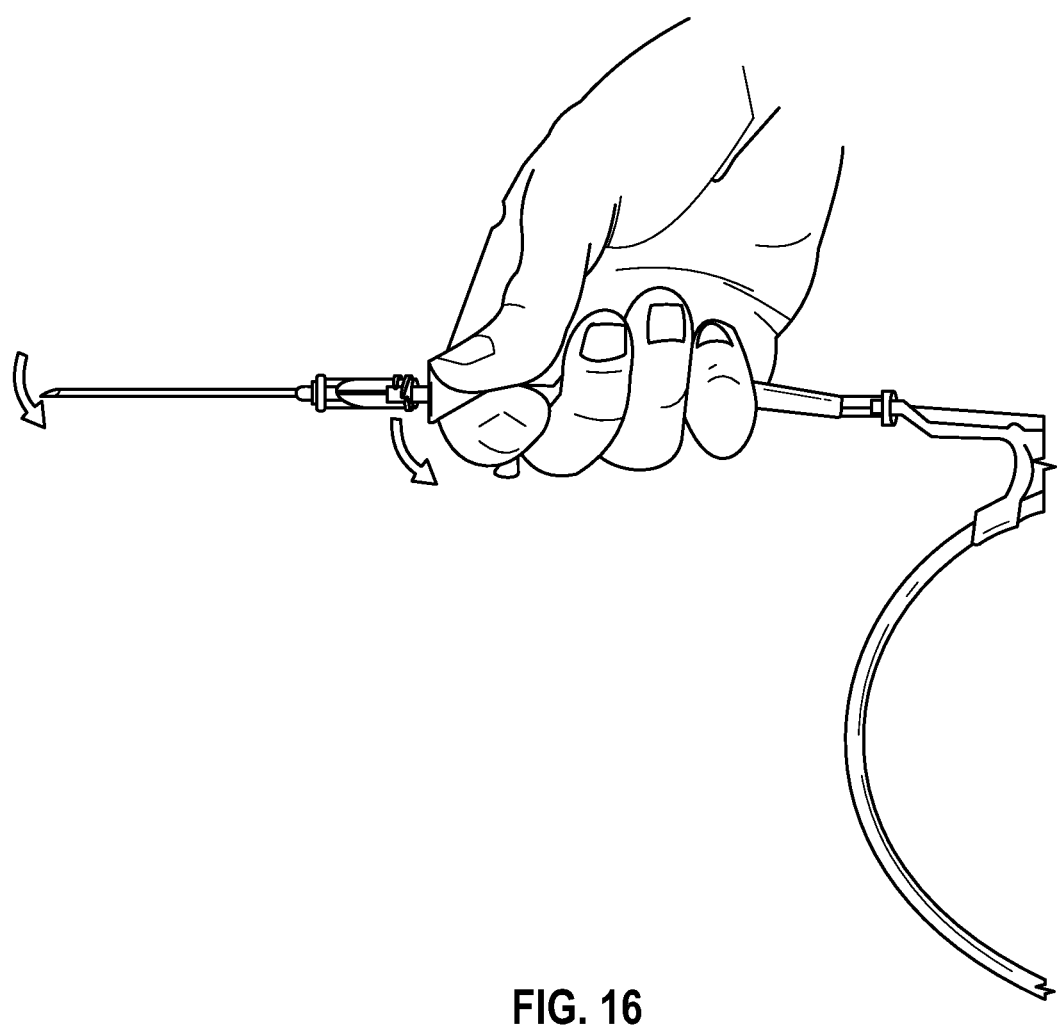

STABILIZER 107: Stabilizer 107 is a unique feature of the WINGUIDE 100. The stabilizer 107 is an elongate protrusion located on and extending away from the lower surface of the WINGUIDE 100. In use, the stabilizer 107 is positioned between the index and middle fingers. The stabilizer 107 is preferably smooth, and may be cylindrical in shape. The stabilizer 107 may have a generally uniform diameter along its length. However, the stabilizer may be tapered. The positioning of the stabilizer 107 allows the clinician to hold the WINGUIDE 100 with the grip of these two fingers only. The stabilizer 107 has a low profile so as not to be obtrusive to the procedure. The WINGUIDE needle tip 116/120 can be moved upwards by rotating the long finger forward on the stabilizer (FIG. 15). The WINGUIDE needle tip 116/120 can also be moved downward by rotating the index finger backward on the stabilizer 107 (FIG. 16).

Once the needle 115 has entered the blood vessel 123 (explained herein below), the WINGUIDE 100 may be stabilized by maintaining a firm grip on the stabilizer 107 between the index and long fingers. It should be noted that the clinician's thumb is not needed for stabilization of the WINGUIDE-needle unit 116/120 at this point. The thumb is used to advance the guidewire 111 while maintaining the WINGUIDE-needle unit 116/120 stationary within the vessel 123. This is a unique feature to the WINGUIDE 100. This eliminates the complication of needle 115 movement during guidewire 111 placement that so often causes difficulty or impossibility of advancement of the guidewire 111.

THUMB TIP RAMP 104: The thumb tip ramp 104 is an optional feature. The thumb tip ramp is an ergonomically contoured surface provided on the upper surface of the WINGUIDE 100 near a distal end thereof. The thumb tip ramp 104 is ramped in a curve that approximates the curve of a thumb in extension. In use, the clinician places his/her thumb on the thumb tip ramp 104 so that the thumb makes contact with the guidewire 111. The clinician advances the guidewire 111 by sliding his/her thumb on the thumb tip ramp 104 from the proximal end toward the distal end while exerting pressure on the guidewire. This allows controlled advancement of guidewire 111 with a single thumb movement up the ramp 104. See FIG. 17.

CLEANING EDGE 105: The WINGUIDE 100 may optionally include a cleaning edge 105 at the junction of the thumb tip ramp 104 and the front (distal) end of the WINGUIDE 100. This is a sharply angled curved contour which is designed to allow the clinician to clean any ultrasound gel or blood from the thumb pad by placing the pad of the thumb on the cleaning edge 105 and pulling back with slight pressure on the cleaning edge 105. This ensures easy advancement of the guidewire 111 even with contamination of the wire slide platform 103 with either blood or sterile ultrasound gel.

CONICAL GUIDEWIRE ACCEPTOR 108: The WINGUIDE 100 is designed to accept the insertion of standard central line guidewires 111. The conical shape of the guidewire acceptor 108 (FIG. 1B) allows the insertion of the guidewire 111 straight from the standard coiled guidewire 119 insertion set up from central line kits.

Figure 17:
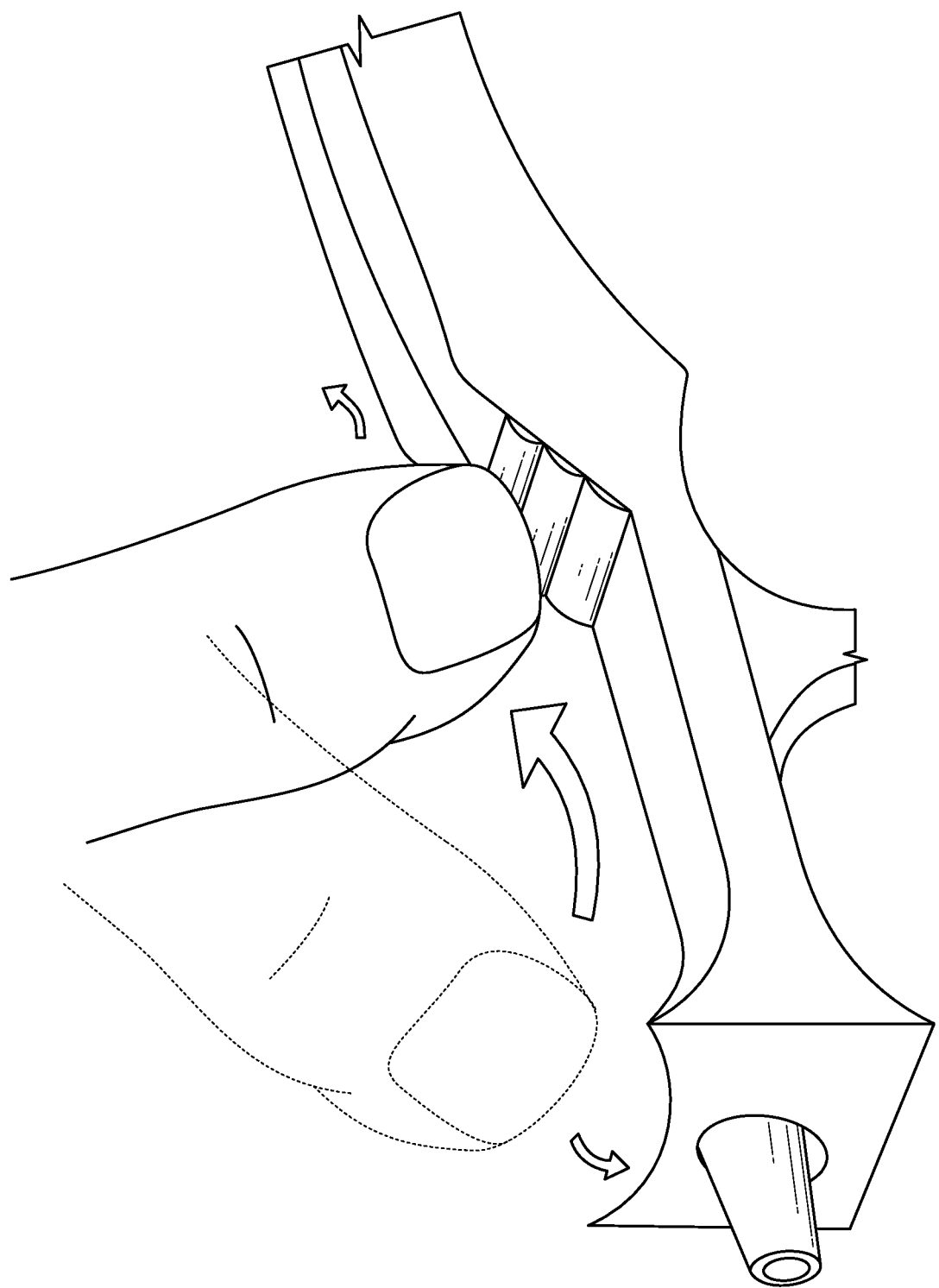
FIG. 17 shows how the thumb can be debrided of ultrasound gel or blood from the thumb pad and the tip of the thumb without aborting the procedure.

WIRE SLIDE PLATFORM 103: The wire slide platform 103 (FIG. 1A & 1B) is a planar surface extending between the thumb tip ramp 104 and the thumb base ramp 102. The guidewire 111 rests on and is advanced along the wire slide platform 103. The wire slide platform 103 facilitates easy thumb advancement of the guidewire 111 (FIG. 17). This platform 103 is preferably constructed from a smooth hard material for maximum guidewire 111 slide. The wire slide platform 103 includes a guidewire runway 127 (FIG. 1E) which is centrally aligned to support the guidewire 111. The guidewire 111 rests on top of the smooth guidewire runway 127. FIG. 1E is a cross-section 126 of the wire slide platform 103.

Groove or gutter 128 may optionally be provided on one or both sides of the guidewire runway 127. Grooves 128 are slightly recessed below the surface of the guidewire runway 127. According to a presently preferred embodiment, a pair of grooves (gutters) 128 are provided, one on each side of the runway 127. In the illustrated embodiment, the grooves 128 are 0.5 mm recessed below the surface of the guidewire runway 127. When view from above, the grooves 128 appear as a v-shaped pattern.

The guidewire runway 127 (FIG. 1E) is designed to maximize contact with the thumb and the guidewire. The aforementioned grooves 128 are designed to express fluid away from the guidewire runway 127 and off of the wire slide platform 103.

FLUTED THUMB BASE RAMP 102: The thumb base ramp 102 is an optional feature which may be fluted or include knurling or other non-slip features to allow the physician to clean the ultrasound gel or blood contamination from the gloved thumb tip FIG. 12. Cleaning of the tip of the thumb is done when the thumb is brought back to the vertical position prior to guidewire 111 advancement. Before guidewire 111 advancement, the tip of the thumb is rubbed down the corrugated fluted thumb tip ramp 102. This allows maximum contact and friction of the gloved thumb tip on the guidewire 111. This is very helpful if there is any contamination from blood or sterile ultrasound gel. The thumb tip ramp 104 and the fluted thumb base ramp 102 in conjunction with the wire slide platform 103 function as a single unit for guidewire 111 advancement. Once the needle is positioned correctly within the vessel 123 and the WINGUIDE-needle unit is stabilized by the stabilizer 107, the thumb can be released from the WINGUIDE 100. The tip of the thumb is brought back to the base of the thumb base ramp 102. At this point the thumb tip is vertical to the wire slide platform 103 and is compressed against the guidewire 111. The thumb tip is then advanced in this fashion until it comes in contact with the thumb tip ramp 104. Now the thumb pad is brought down to a gradual horizontal position and the pad of the thumb is advanced over the thumb tip ramp 104. During this procedure the contact of the thumb with the guidewire 111 moves from the tip across the thumb pad and finally to the interphalangeal joint of the thumb. During this motion the guidewire 111 is actually advanced significantly more than just using the thumb tip alone. This is a unique feature of the WINGUIDE 100. It allows the physician to advance a significant section of guidewire 111 into the vessel 123 with a single stroke. This mitigates further possible needle tip 116/120 movement which is more likely to occur with more maneuvering. This lowers the risk of misplacing the guidewire 111.

GUIDEWIRE CHANNEL 109: The guidewire channel 109 (FIG. 1B & 2B) of the WINGUIDE 100 is designed to allow the guidewire 111 to be loaded into the device. It prevents contact with the palm of the hand and therefore minimizes friction during advancement of the guidewire 111. It is designed to be in the same axis as the lumen of the needle 120/121. This minimizes friction as well.

Figure 9:
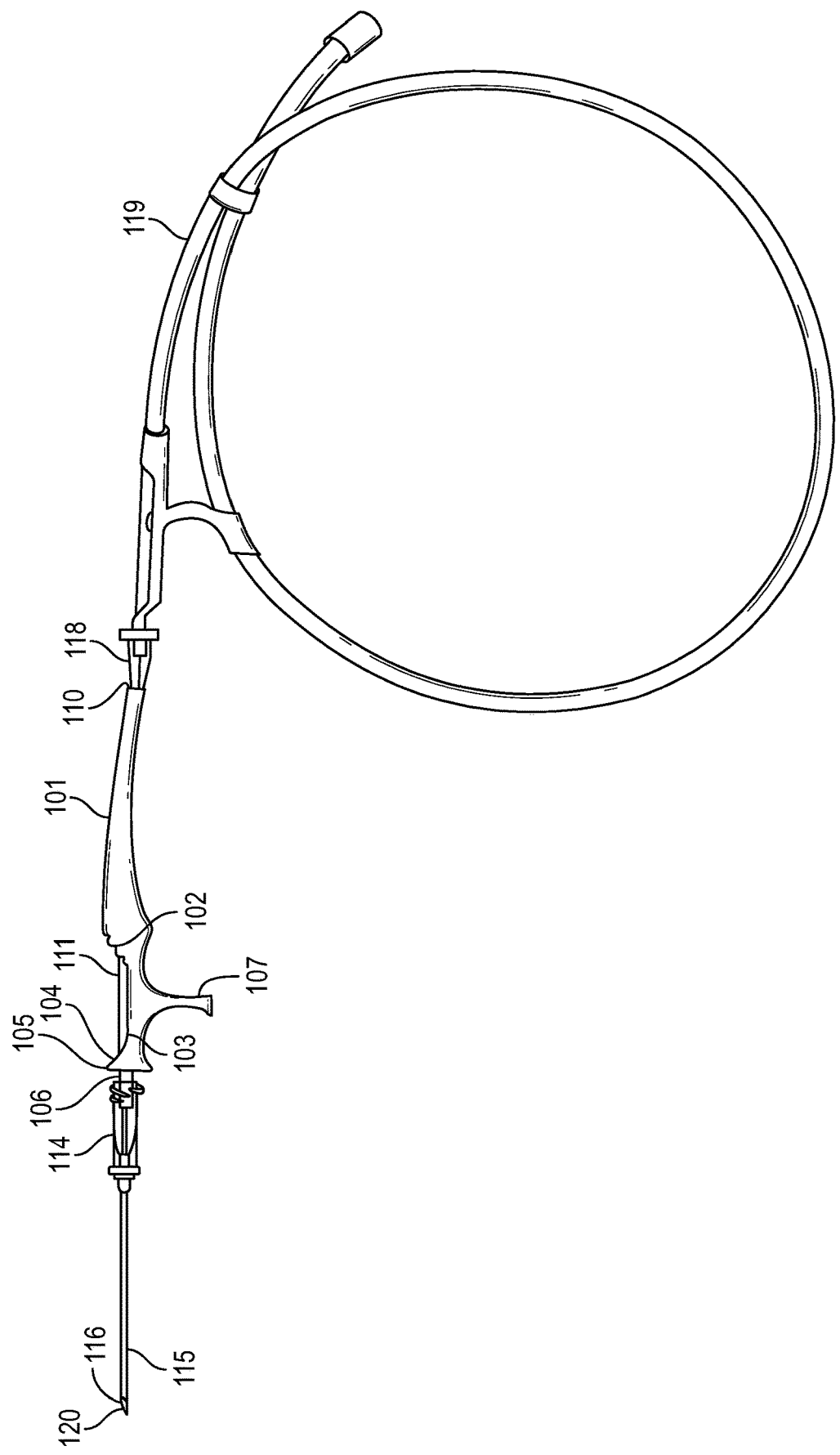
FIG. 9 shows the device shown in FIG. 1A or FIG. 2A with the guidewire coil 119 and needle 115 attached.
Figure 11:
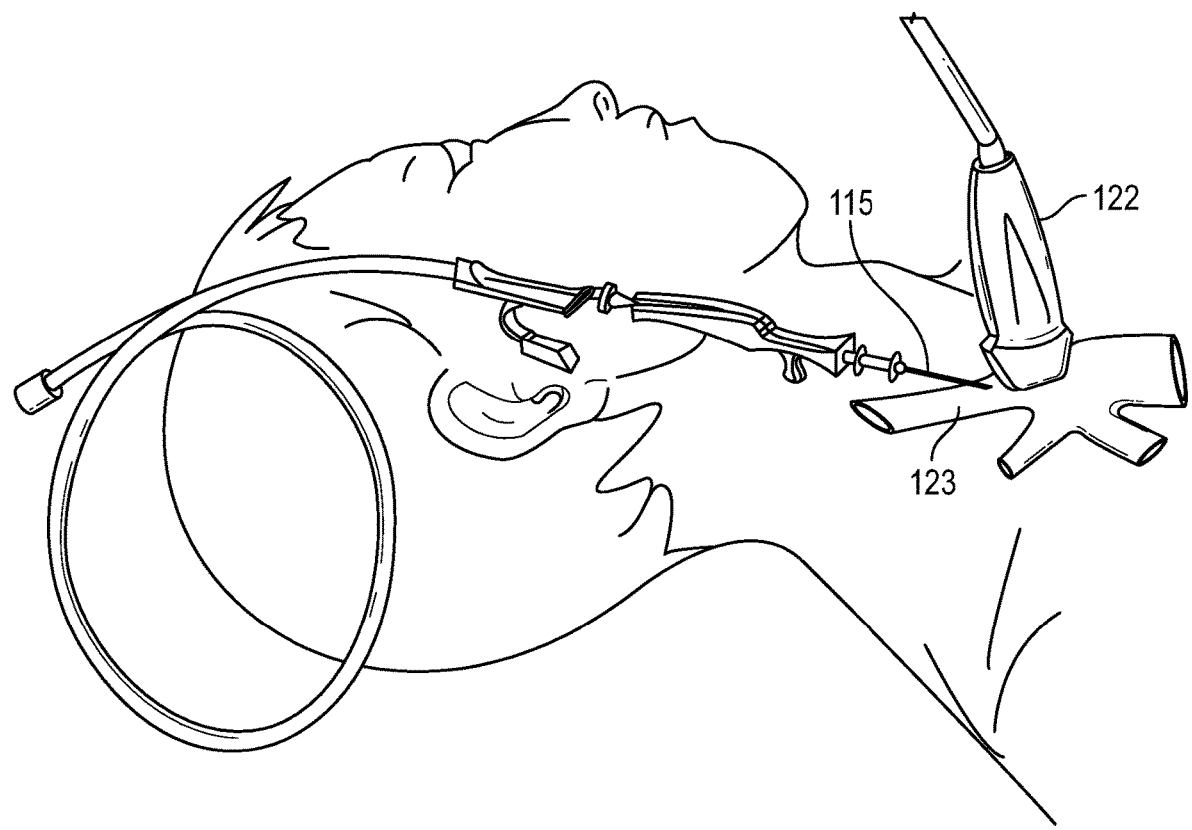
FIG. 11 is an illustration showing how the needle attached is used to puncture the skin and advance towards the lumen of the vein using the device shown in FIG. 1A or FIG. 2A.

The WINGUIDE 100 is an ergonomically designed needle guide used to facilitate cannulation of a blood vessel. A needle 115 is attached to Luer slip tip 106 of the WINGUIDE 100 and a conventional guidewire 111 is then threaded into the WINGUIDE-needle unit via guidewire feeder tip receiver 110 (FIG. 1B & 2B) and held firmly in place by the pressure of the thumb. The clinician performs the canalization procedure using ultrasound transducer 122 (FIG. 11). The ultrasound transducer 122 is held in the non-dominant hand and the WINGUIDE 100 (FIG. 1) is placed in the dominant hand. FIG. 9 shows needle 115 attached to the Luer slip tip 106 located on the proximal end of the WINGUIDE 100 with the coiled guidewire 119 attached to the WINGUIDE 100 via of the guidewire feeder tip receiver 110. Once the clinician visualizes the venous access of the needle on ultrasound, the WINGUIDE 100 is used to advance the guidewire 111 without losing visualization from ultrasound. Once the guidewire 111 is threaded through needle lumen 120/121 into blood vessel 123 (FIG. 11) the procedural difficulty drops precipitously.

The conventional wire-in-needle technique is technically difficult to perform. Use of the WINGUIDE 100 greatly simplifies the placement of a central line by the WIN technique with direct visualization via ultrasound. The WINGUIDE 100 of the present invention solves two problems.

First, advancement of the wire-in-needle unit is greatly simplified with the use of the WINGUIDE 100 versus advancing a wire in needle while grasping the needle hub. Second, as soon as the vessel 123 is penetrated by the needle, the WINGUIDE 100 can be quickly and easily stabilized without losing ultrasound visualization, ensuring the guidewire 111 can be definitively visualized as it enters the vessel lumen.

Arterial Access

Figure 2A:
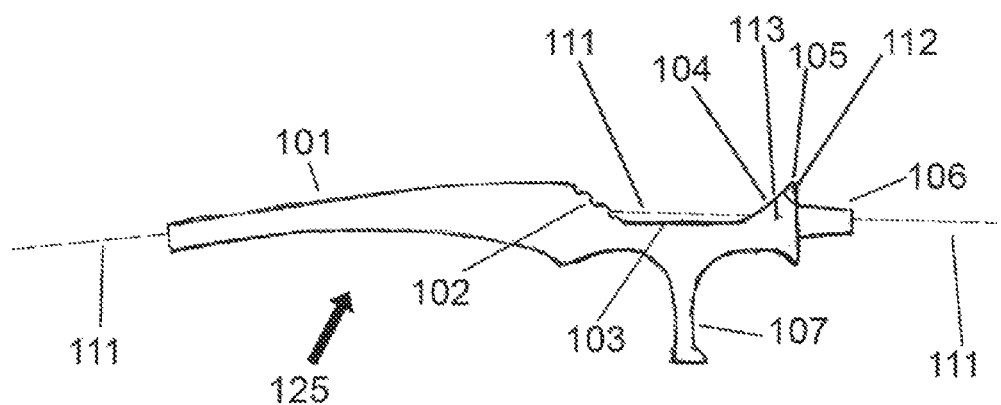
FIGS. 2A-2D are side, top, front and back views of WINGUIDE Arterial 125.
Figure 2B:
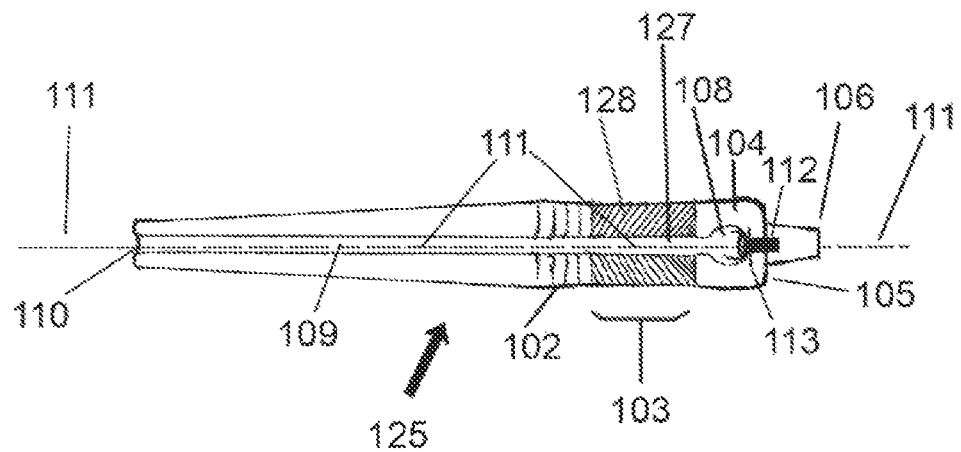
Figures 2C, 2D:
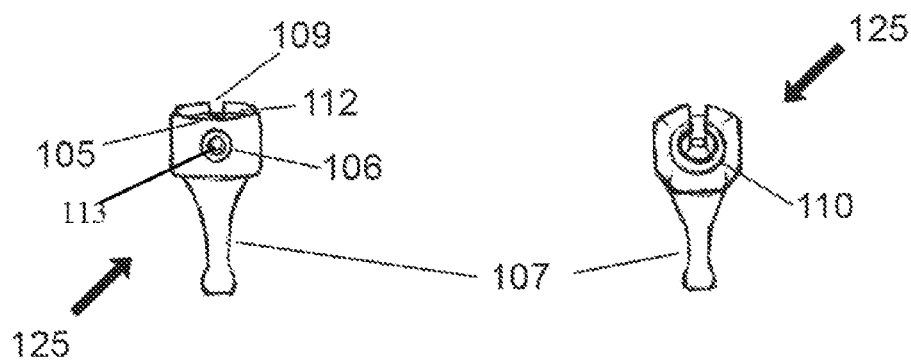

The aforementioned WINGUIDE 100 wire-in-needle technique is for venous access. However, the WINGUIDE 100 may also be used for arterial access. While it is possible to use the WINGUIDE 100 for arterial access, certain enhancements may be useful. FIG. 2 shows WINGUIDE arterial 125 which is similar to the WINGUIDE 100 (FIGS. 1A-1E) but includes a couple optional features. WINGUIDE Arterial 125 may include an optional backflow preventer 113 (FIG. 2B, 2C) to prevent the guidewire 111 from getting contaminated with blood as it sits on wire slide platform 103. The backflow preventer 113 may be a gasket or the like which at least partially surrounds the guidewire 111 and prevents blood from wicking up the guidewire in a proximal direction (toward the clinician). The WINGUIDE Arterial 125 may optionally be provided with a clear plastic flash reservoir 112 (FIG. 2B, 2C) in the center of the thumb tip ramp 104. This reservoir 112 is uniquely designed to show the flash of arterial blood when the lumen of the needle enters the artery thus confirming placement. With the flash reservoir 112 the WINGUIDE Arterial 125 may be used with or without ultrasound transducer 122 guidance.

Instructions for Use—Applicable to Both WINGUIDE and WINGUIDE Arterial

Figure 4:
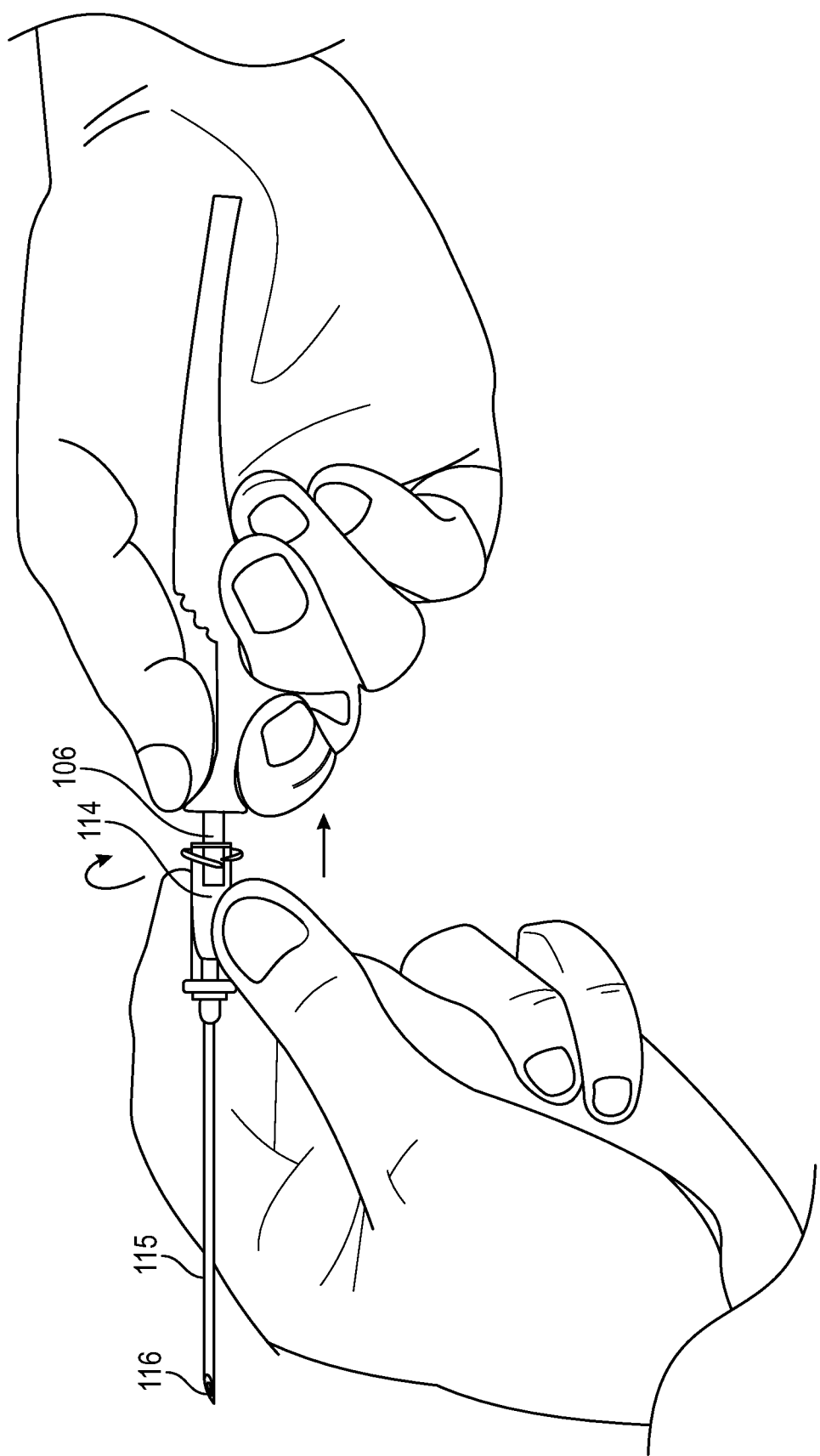
FIG. 4 is an illustration showing how the needle hub is attached to the Luer slip tip 106.

Step 1: Grasp needle hub 114 and secure needle 115 to Luer slip tip 106 of WINGUIDE 100 with twisting motion. Align bevel of needle 116 to desired position. (FIG. 4)

Step 2: Take guidewire coil 119 and insert guidewire feeder tip 118 into the conical guide wire acceptor 108 of the WINGUIDE 100. (FIG. 5)

Figure 6:
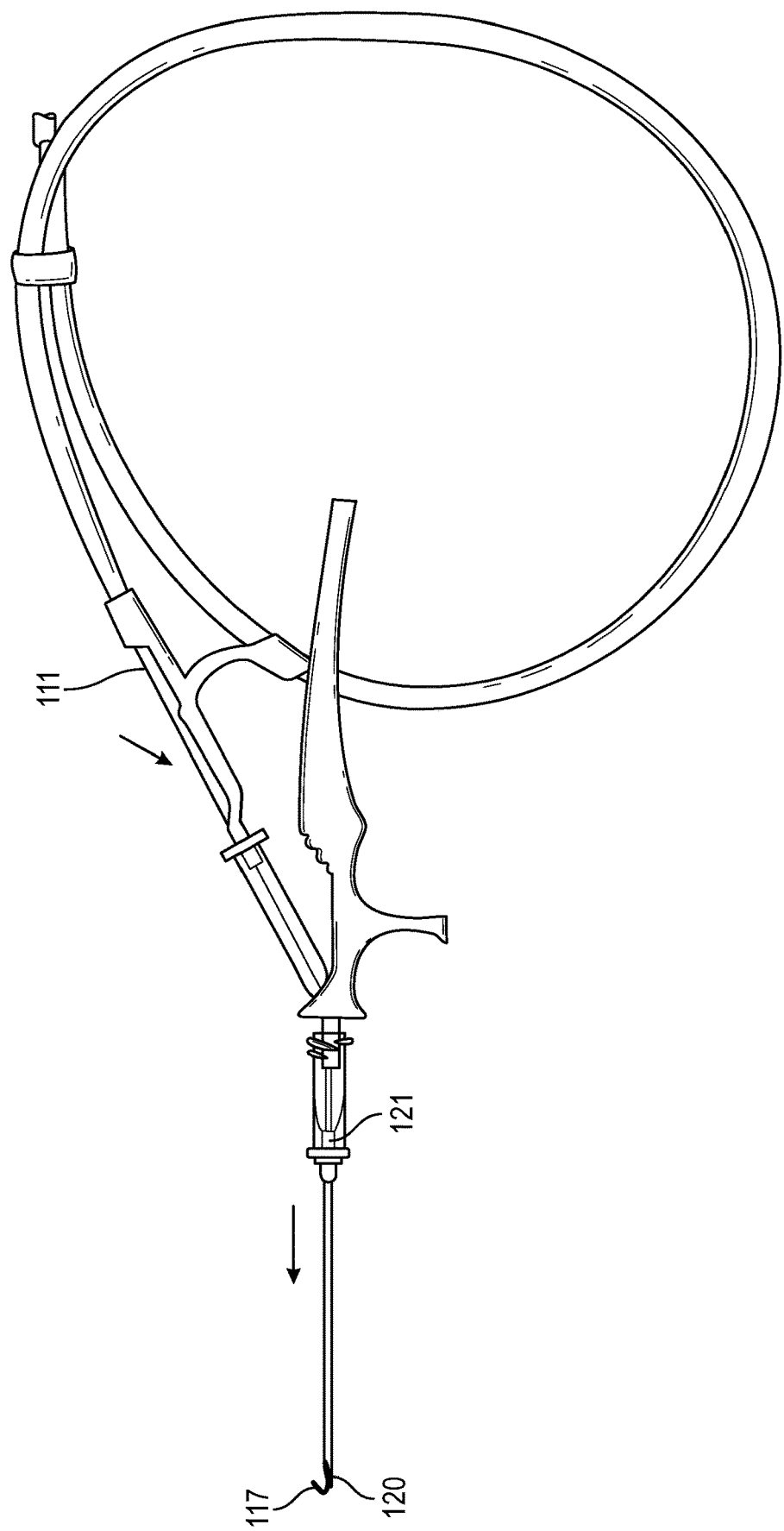
FIG. 6 is an illustration showing how the guidewire is advanced through the needle lumen in the device shown in FIG. 1A or FIG. 2A.

Step 3: Slide guidewire 111 into lumen of needle 121 until J tip 117 (FIG. 3B & FIG. 6) of the guidewire 111 comes out the distal end of the needle 120. (FIG. 6)

Figure 7:
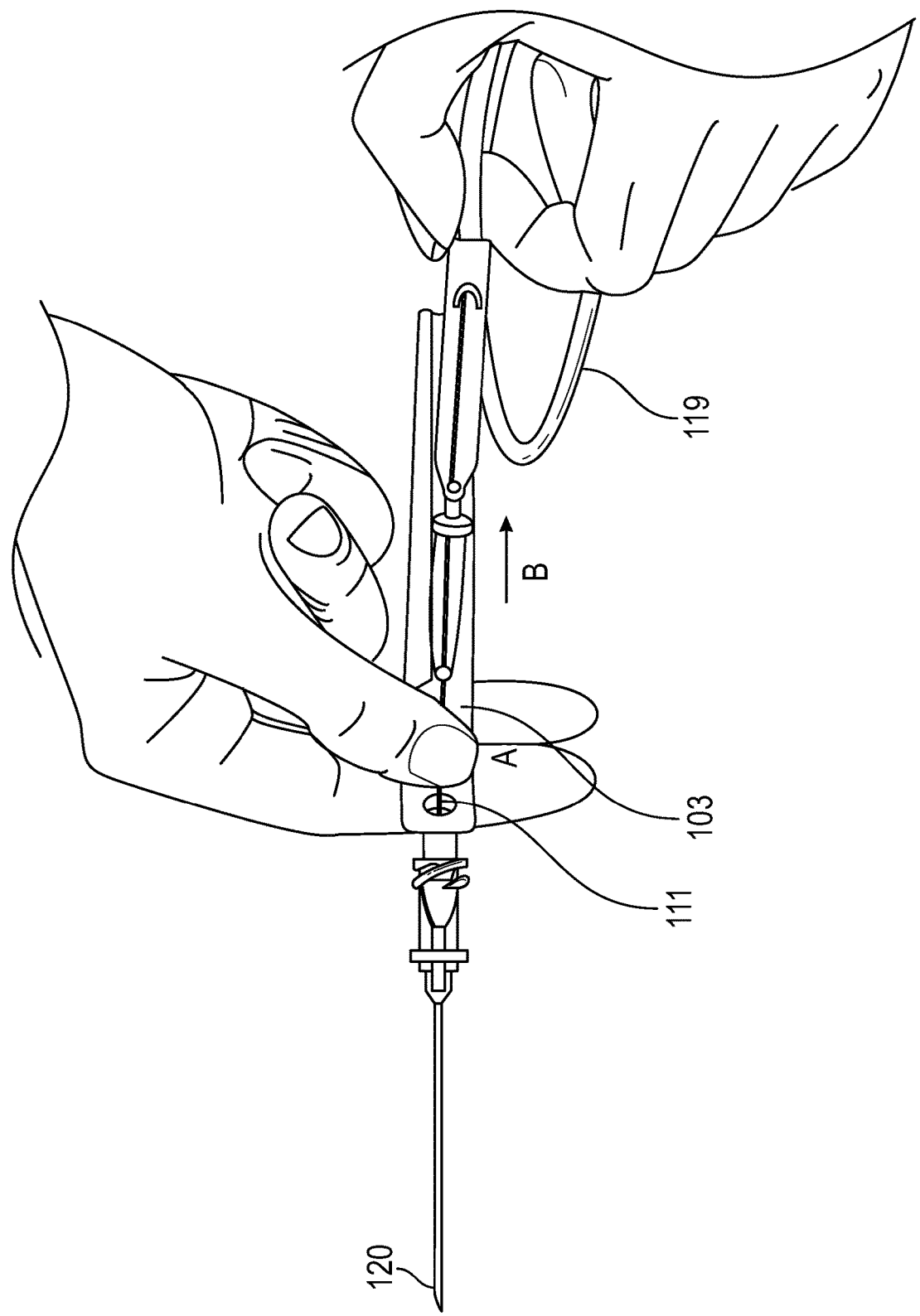
FIG. 7 is an illustration showing how the guidewire length is adjusted in the device shown in FIG. 1A or FIG. 2A.

Step 4: Slide J tip 117 back into needle 115 so that it is just inside the needle lumen 120. Press guidewire 111 on wire slide platform 103 with non-dominant thumb to hold guidewire 111 in place on the wire slide platform 103 (A). Pull guidewire coil 119 back to rear of WINGUIDE thus exposing excess guidewire 111 to be laid into guidewire channel 109 (direction arrow B). (FIG. 7)

Figure 8:
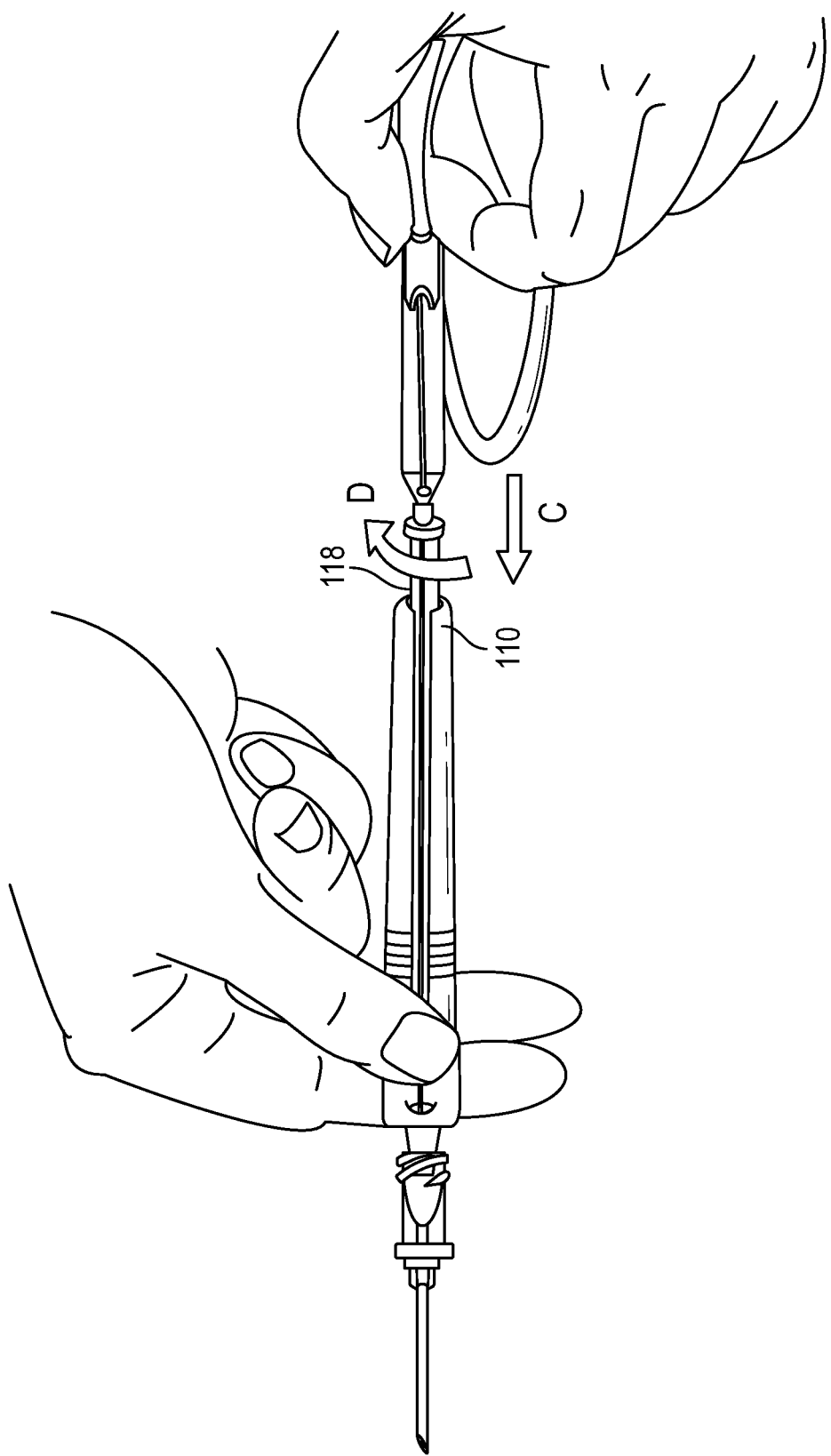
FIG. 8 is an illustration showing how guidewire feeder tip 118 is into guidewire feeder tip receiver 110.

Step 5: Insert guidewire feeder tip 118 into guidewire feeder tip receiver 110 of the WINGUIDE 100 (C) and twist into place (D). (FIG. 8)

Step 6: The WINGUIDE-needle-guidewire unit is ready for use. (FIG. 9)

Figure 10:
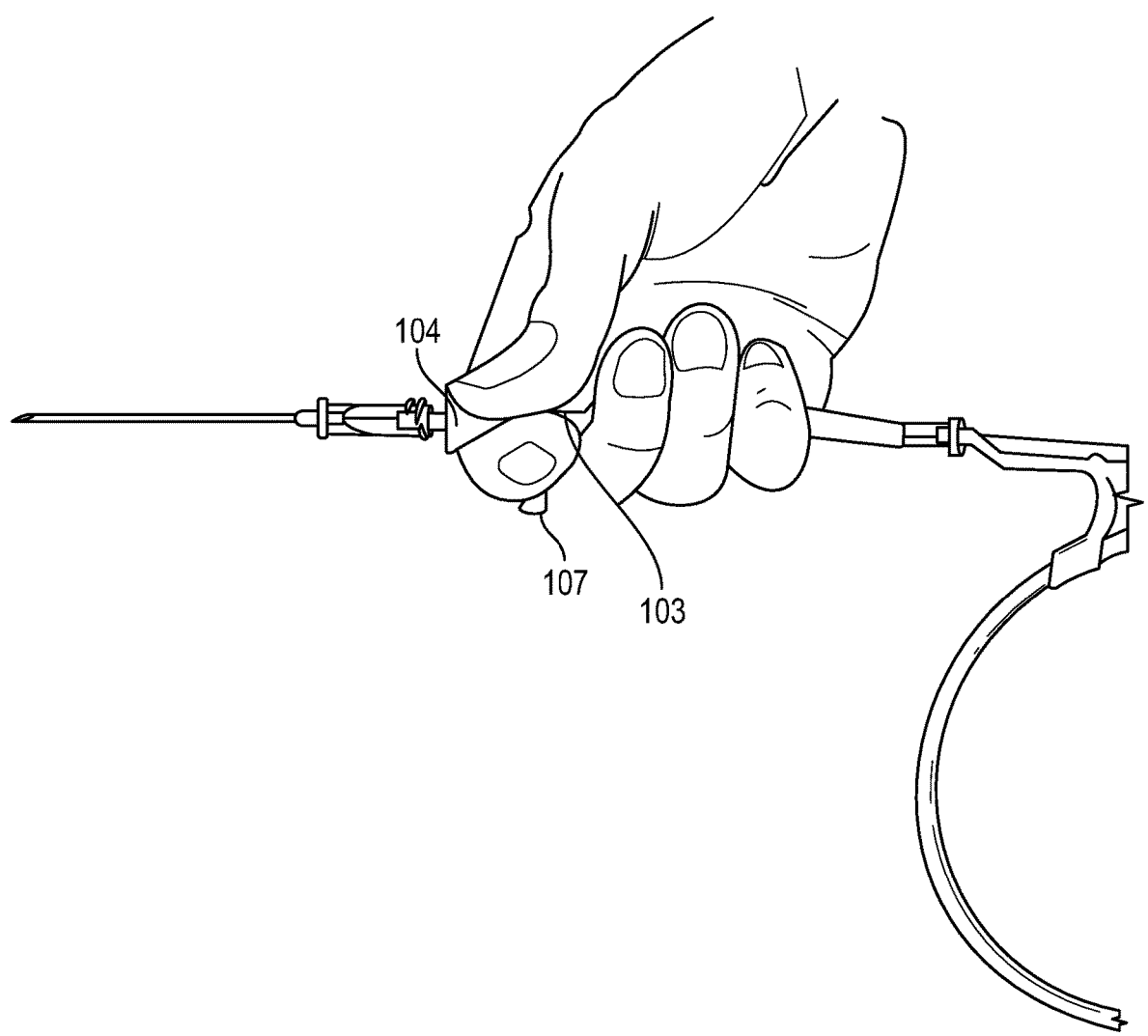
FIG. 10 is an illustration showing how the device shown in FIG. 1A

Step 7: Grasp the WINGUIDE 100 for insertion by placing the stabilizer 107 between the long and index fingers. Set the thumb on the thumb tip ramp 104 and compress guidewire 111 with the thumb onto the wire slide platform 103. The WINGUIDE 100 is now loaded with the guidewire 111 and ready for vein 123 cannulation. (FIG. 10)

Step 8: Identify the vein 123 to be cannulated with the ultrasound transducer 122. Use the needle attached to the WINGUIDE 100 to puncture the skin and advance towards the lumen of the vein 123. Insert needle 115 into the lumen of the vein 123. (FIG. 11)

Figure 12:
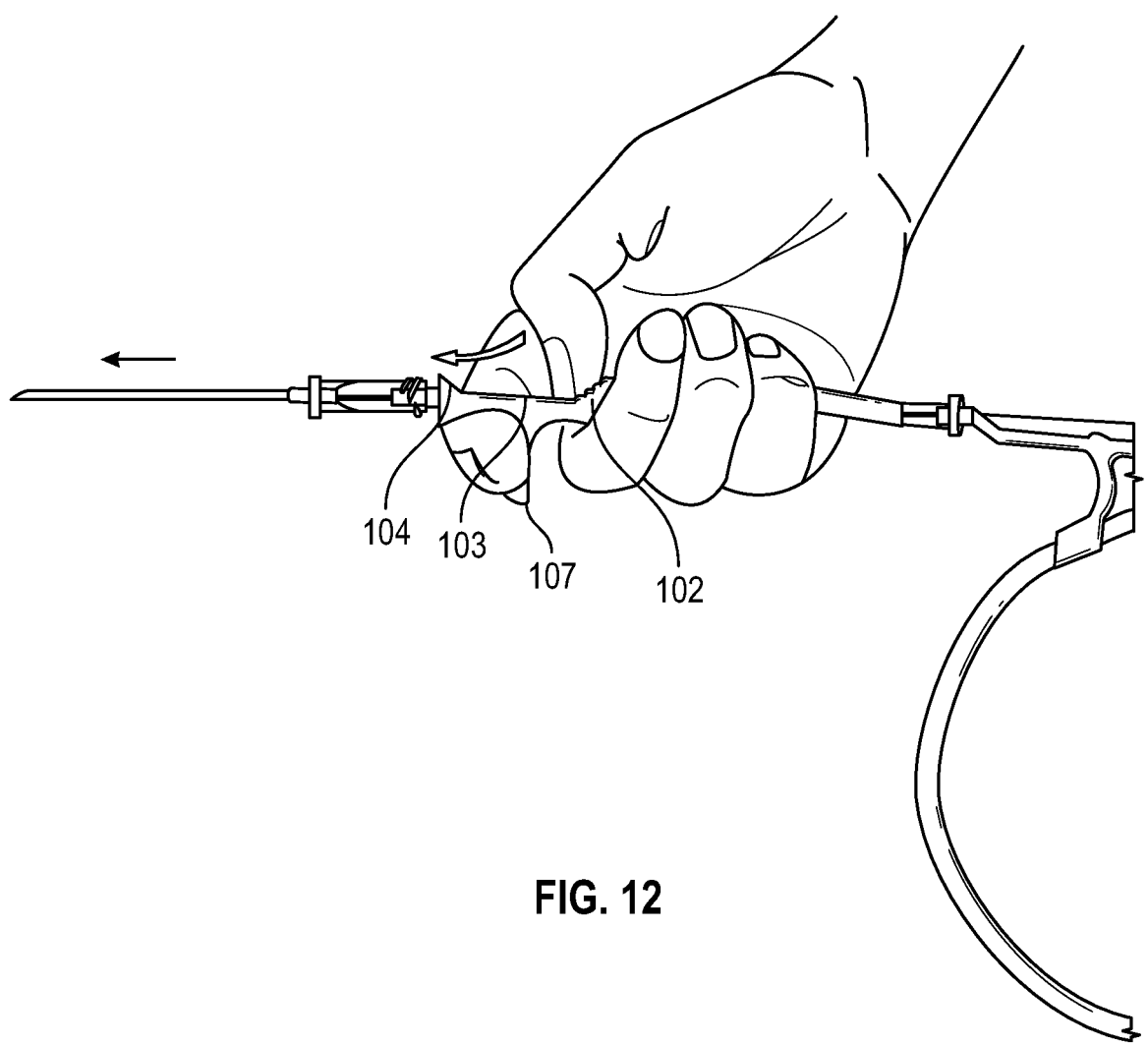
FIG. 12 is an illustration showing how the device shown in FIG. 1A

Step 9: Stabilize the WINGUIDE 100 by compressing the long and index fingers onto the stabilizer 107 and place the thumb tip in a vertical position at the fluted thumb base 102. Compress the guidewire 111 on the wire slide platform 103 with the thumb tip. Advance the guidewire 111 on the wire slide platform 103 to the thumb tip ramp 104. (FIG. 12)

Figure 13:
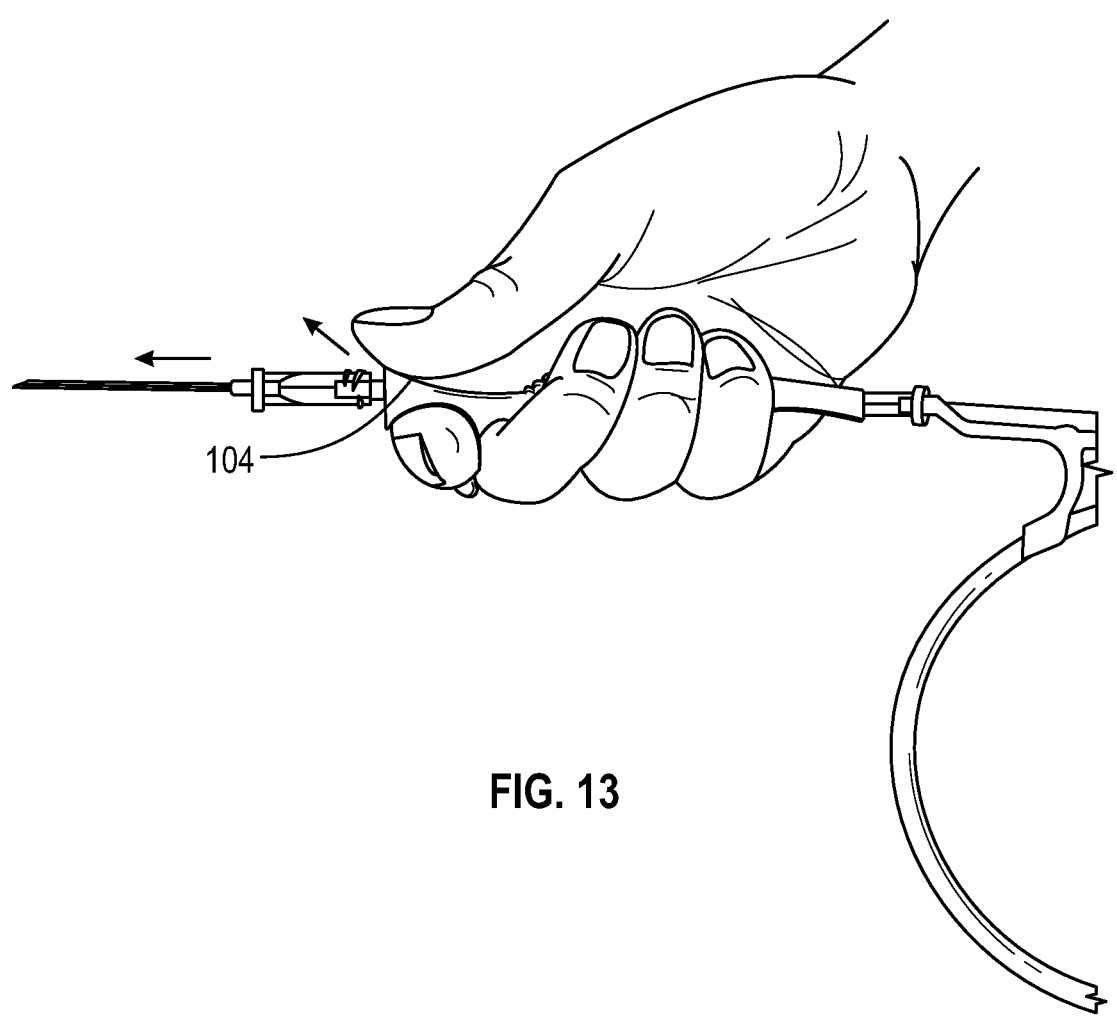
FIG. 13 is an illustration showing how guidewire is advanced into a blood vessel using the device shown in FIG. 1A or FIG. 2A.

Step 10: Advance the thumb tip and thumb pad up the thumb tip ramp 104 further advancing the guidewire 111 into the lumen of the vein 123. Repeat steps 9 and 10 as needed to advance as much guidewire 111 as needed. (FIG. 13)

Figure 14:
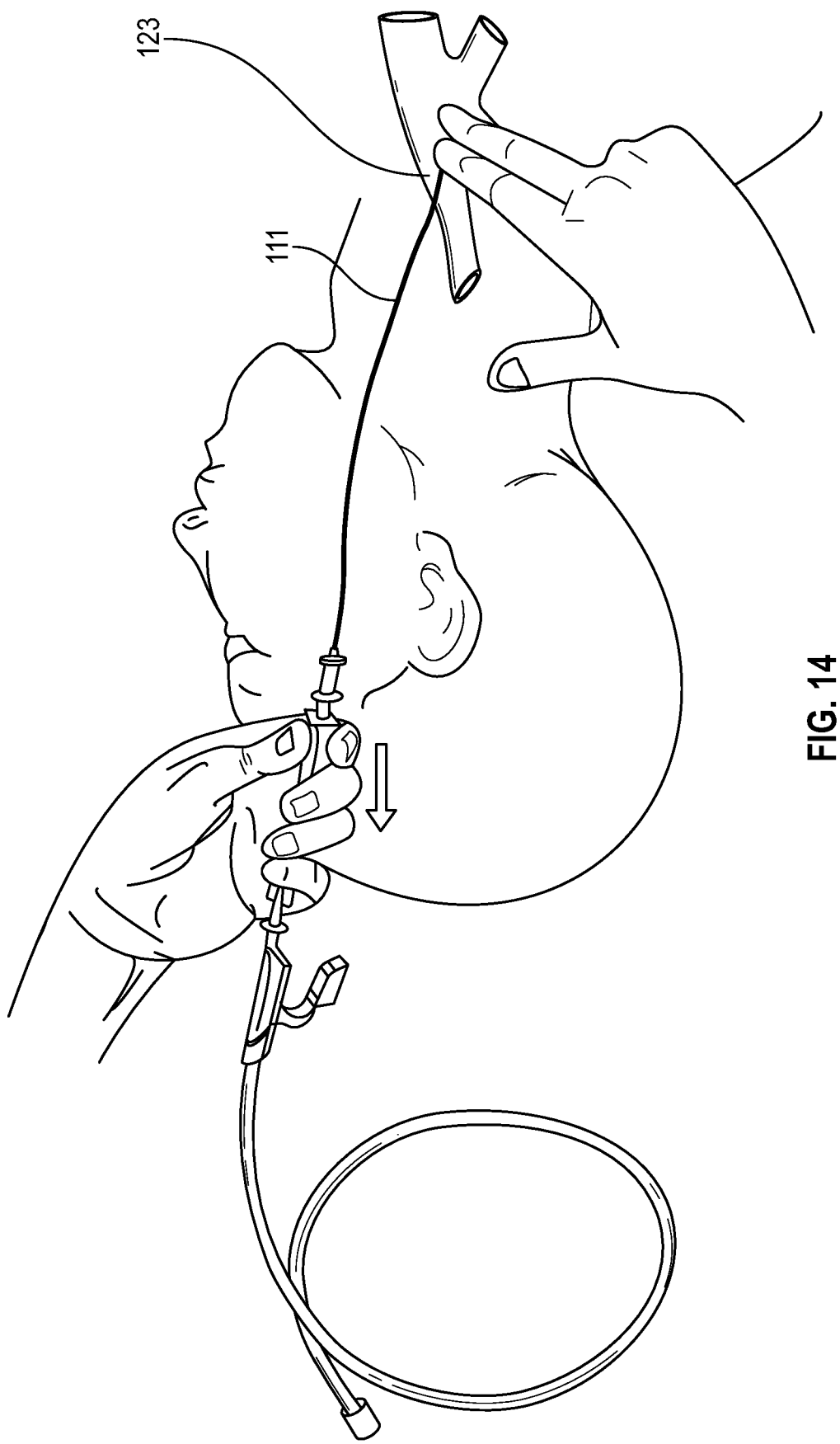
FIG. 14 is an illustration showing how needle is withdrawn from the blood vessel after the guidewire is inserted using the device shown in FIG. 1A or FIG. 2A.

Step 11: Release thumb pressure on guidewire 111. Slowly back the WINGUIDE-needle unit out, while compressing the guidewire 111 on the skin with the other hand. This exposes the guidewire 111 entering the skin and vein 123. (FIG. 14)

Step 12: Remove the WINGUIDE needle unit. Complete central line placement as per central line manufacturer's' product instructions. (FIG. 15)

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

The invention claimed is:

1. A device for facilitating placement of a central line in a patient, said device comprising:
    a housing having proximal and distal ends and a central portion therebetween, said housing having an upper portion and a lower portion;
    the proximal end of the housing forming a handgrip, the housing having at least one of a channel and a through hole extending from a proximal most end of the housing to the central portion of the housing, wherein the channel or through hole is sized to receive and support opposing lateral sides of an unsheathed guidewire;
    a feeder tip receiver provided on a proximal end of the handgrip in communication with the channel or through hole in said handgrip;
    a stabilizer comprising an elongate, cylindrical protrusion, said stabilizer located on and extending away from the lower portion of said housing and generally centered beneath the central portion of the housing, wherein the stabilizer is positioned and sized so as to allow a clinician to hold the device during use with a grip of the index and middle fingers;
    a luer slip tip provided on the distal end of the housing, said luer slip tip having a mounting portion for attachment to a needle hub assembly, said luer slip tip having a lumen aligned with the channel or through hole in said handgrip; and
    a wire slide platform provided on the central portion of the housing, a top surface of the unsheathed guidewire is exposed a full length of the wire slide platform such that a user can longitudinally advance/retract the unsheathed guidewire by applying force along the top surface of the unsheathed guidewire, wherein the stabilizer is located underneath the wire slide platform.

2. The device of claim 1 further comprising a thumb base ramp provided on the housing proximate a proximal end of the wire slide platform.

3. The device of claim 2, wherein the thumb base ramp angles downward towards the wire slide platform.

4. The device of claim 3, wherein the thumb base ramp includes non-slip features.

5. The device of claim 1, further comprising a thumb tip ramp provided on the housing proximate a distal end of the wire slide platform.

6. The device of claim 5, wherein the thumb tip ramp angles upward away from the wire slide platform.

7. The device of claim 5, further comprising a cleaning edge provided adjacent the thumb tip ramp.

8. The device of claim 5, further comprising a transparent flashback reservoir in the thumb tip ramp, the reservoir is in fluid communication with the luer slip tip lumen.

9. The device of claim 1, wherein the needle hub assembly includes a hollow sharpened needle having a lumen extending therethrough, said hollow sharpened needle attached to a hub, said hub removably attached to the luer slip tip.

10. The device of claim 1, further comprising an unsheathed guidewire acceptor adjacent a distal end of the wire slide platform and having a lumen aligned and in communication with said luer slip tip lumen and the channel or through hole in said housing.

11. The device of claim 10, wherein the guidewire acceptor is funnel shaped with a wide mouth which tapers to a narrow lumen, wherein the guidewire acceptor is configured to receive the unsheathed guidewire fed from the feeder tip receiver through the handgrip, on the wire slide platform and out the luer slip tip lumen.

12. The device of claim 1, wherein a thickness of the handgrip gradually increases from the proximal end of the handgrip to a distal end of the handgrip.

13. The device of claim 1, further comprising a backflow preventer provided in fluid communication with the luer slip tip lumen, the backflow preventer comprising a gasket configured to surround and engage the unsheathed guidewire.

14. A method for using the device of claim 1, comprising:
    providing the device according to claim 1;
    the device including a guidewire acceptor adjacent a distal end of the wire slide platform and having a lumen aligned and in communication with said luer slip tip lumen;
    providing a needle assembly having a hub attached to a hollow sharpened needle with a lumen extending therethrough;
    attaching the hub of the needle assembly to the luer slip tip;
    providing a guidewire assembly having a guidewire in a coiled sheath, said coiled sheath including a guidewire feeder tip;
    inserting the guidewire feeder tip into the guidewire acceptor;
    advancing the guidewire from the coiled sheath through the guidewire feeder tip into the needle lumen; and
    removing the guidewire feeder tip from the guidewire acceptor without withdrawing the guidewire from the needle lumen and inserting the guidewire feeder tip into the feeder tip receiver.

15. The method of claim 14, further comprising the steps of:
    identify a blood vessel to be cannulated using an ultrasound transducer;
    grasping the device with a user's hand and using the needle to puncture the skin and advance towards a lumen of a vein while visualizing using ultrasound;
    inserting the needle into the lumen of the vein.

16. The method of claim 15, further comprising the steps of:
    stabilizing the device by compressing long and index fingers of the user's hand onto the stabilizer and placing a thumb tip of the user's hand in a vertical position at a thumb base ramp;
    compressing the guidewire on the wire slide platform with the thumb tip; and
    advancing the guidewire on the wire slide platform to the thumb tip ramp.

17. The method of claim 16, further comprising the step of:
    advancing the thumb tip up the thumb tip ramp to advance the guidewire into the lumen of the vein.

18. The method of claim 17, further comprising the steps of:
    releasing thumb pressure on the guidewire;

and slowly backing the needle out of the skin, while compressing the guidewire on the skin with the other hand to expose the guidewire entering the skin and the vein.

* * * * *